US010231714B2

(12) United States Patent
Gao et al.

(10) Patent No.: US 10,231,714 B2
(45) Date of Patent: Mar. 19, 2019

(54) ACTUATOR OF MEDICAL DEVICE

(71) Applicant: Johnson Electric S.A., Murten (CH)

(72) Inventors: Jian Dong Gao, Shenzhen (CN); Wai To Li, Hong Kong (CN)

(73) Assignee: JOHNSON ELECTRIC INTERNATIONAL AG, Murten (CH)

( * ) Notice: Subject to any disclaimer, the term of this patent is extended or adjusted under 35 U.S.C. 154(b) by 537 days.

(21) Appl. No.: 14/866,289

(22) Filed: Sep. 25, 2015

(65) Prior Publication Data

US 2016/0089120 A1 Mar. 31, 2016

(30) Foreign Application Priority Data

Sep. 29, 2014 (CN) .......................... 2014 1 0515208

(51) Int. Cl.
*A61B 10/02* (2006.01)

(52) U.S. Cl.
CPC ...... *A61B 10/0233* (2013.01); *A61B 10/0275* (2013.01); *A61B 2010/0208* (2013.01)

(58) Field of Classification Search
CPC ........ A61B 2010/0208; A61B 10/0233; A61B 10/0275
See application file for complete search history.

(56) References Cited

U.S. PATENT DOCUMENTS

| | | | | |
|---|---|---|---|---|
| 5,842,999 A | * | 12/1998 | Pruitt ................. | A61B 10/0275 600/562 |
| 5,989,197 A | | 11/1999 | Avaltroni | |
| 6,126,617 A | | 10/2000 | Weilandt et al. | |
| 2001/0009979 A1 | * | 7/2001 | Weilandt ............ | A61B 10/0266 600/567 |
| 2004/0225229 A1 | * | 11/2004 | Viola ................. | A61B 10/0275 600/564 |
| 2006/0155210 A1 | * | 7/2006 | Beckman ........... | A61B 10/0275 600/567 |
| 2007/0032741 A1 | * | 2/2007 | Hibner ............... | A61B 10/0275 600/566 |

(Continued)

FOREIGN PATENT DOCUMENTS

| | | | |
|---|---|---|---|
| WO | WO 0224077 A1 | * 3/2002 | ........ A61B 10/0275 |
| WO | WO 02/24077 A1 | 5/2014 | |
| WO | WO 2014/081812 A1 | 5/2014 | |

OTHER PUBLICATIONS

Search Report dated Feb. 15, 2016 in corresponding EP patent application No. 15 18 6766 (6 pgs.).

*Primary Examiner* — Sean P Dougherty
*Assistant Examiner* — Nicholas E Kolderman
(74) *Attorney, Agent, or Firm* — Muncy, Geissler, Olds & Lowe, P.C.

(57) ABSTRACT

An actuator for a medical device includes a housing, a driving unit mounted in the housing, a first moving unit slidably mounted in the housing and movable by the driving unit. The first moving unit includes a movable first car, an spring with two ends thereof abutting the housing and first car, respectively, and a lock formed between the driving unit and first car. The lock includes a first snap and a first protrusion detachably engagable with the first snap. One of the first snap and first protrusion is formed on the first car, and the other is formed on the driving unit. When the first protrusion disengages from the first snap, the spring moves the first car relative to the housing.

11 Claims, 6 Drawing Sheets

(56) References Cited

U.S. PATENT DOCUMENTS

| | | | | |
|---|---|---|---|---|
| 2008/0214955 A1* | 9/2008 | Speeg | ............... | A61B 10/0275 600/567 |
| 2012/0265095 A1* | 10/2012 | Fiebig | ............... | A61B 10/0275 600/567 |
| 2013/0165815 A1* | 6/2013 | Zinn | ................. | A61B 10/0275 600/567 |
| 2015/0238171 A1* | 8/2015 | Shabaz | ............. | A61B 10/0275 600/567 |

* cited by examiner

ACTUATOR OF MEDICAL DEVICE

CROSS REFERENCE TO RELATED APPLICATIONS

This non-provisional patent application claims priority under 35 U.S.C. § 119(a) from Patent Application No. 201410515208.7 filed in The People's Republic of China on Sep. 29, 2014, the entire contents of which are hereby incorporated by reference.

FIELD OF THE INVENTION

This invention relates to medical equipment, and in particular, to an actuator or driving device of a biopsy device such as a liver biopsy device.

BACKGROUND OF THE INVENTION

Biopsy is a medical test involving sampling of cells or tissues for examination. It is the medical removal of tissue from a living subject to determine the presence or extent of a disease. Biopsy is most commonly performed for insight into possible cancerous and inflammatory conditions. It is accurate and reliable. A biopsy device generally includes a needle and a needle tube covering the needle. In use, the needle tube is firstly inserted into the body of the patient to cover the tissue, and then the needle is inserted into the needle tube to a predetermined depth to cut the tissue. The cut tissue is received in the needle tube, and removal from the patient along with the needle tube.

For the above biopsy device, moving of the needle and needle tube are respectively controlled by two actuators and two springs, which is not only complex in structure, but also complex in operation. In addition, a preloading force on the spring is not easy to control.

SUMMARY OF THE INVENTION

Hence there is a desire for an actuator for a biopsy device which is more simple in construction and/or easier to use.

Accordingly, in one aspect thereof, the present invention provides an actuator of a medical device, comprising: a housing; a driving unit mounted in the housing; a first moving unit mounted in the housing and being capable of sliding relative to the housing under the driving of the driving unit, the first moving unit comprising a movable first carriage; a spring with two ends thereof abutting the housing and first carriage, respectively; and a first lock formed between the driving unit and first carriage, the first lock comprising a first snap and a first protrusion being detachably engagable in the first snap, one of the first snap and first protrusion being formed on the first carriage, and the other one of the first snap and first protrusion being formed on the driving unit; wherein when the first protrusion disengages from the first snap, the spring moves the first carriage relative to the housing.

Preferably, a second moving unit being capable of sliding relative to housing, is provided, the seconding moving unit comprising a movable second carriage, a second lock formed between the first and second carriages, the second lock comprising a second protrusion formed on one of the first and second carriages, and a second snap formed on the other one of the first and second carriage, the second protrusion being detachably engagable in the second snap, wherein when the second protrusion is engaged with the second snap, the first and second carriages are connected together and spaced from each other a predetermined distance; and when the second protrusion is disengaged from the second snap, the first and second carriages can slide relative to each other.

Preferably, the second snap defines an aperture and a slot communicating with the aperture, the slot extending along a deformation direction of the spring, a bottleneck being formed at a junction of the aperture and slot, wherein when the second protrusion is engaged with the second snap, the second protrusion is captured within the aperture; and when the second protrusion is disengaged from the second snap, the second protrusion is disposed in the slot.

Preferably, the housing forms a pin, a guiding rail extends from the first carriage, the guiding rail defines a groove which extends in the deformation direction of the spring and though one end of the guiding rail facing the pin, the spring is received in the groove, a length of the spring is not less than that of the groove, one end of the spring abuts the pin, and the other end of the spring abuts a closed end of the groove in the guiding rail.

Preferably, the driving unit comprises a motor, a leadscrew, and a gear box connected between the motor and the leadscrew, the other one of the first snap and first protrusion being screwed on the leadscrew.

Alternatively, the driving unit comprises a motor, a leadscrew, a gear box connected between the motor and leadscrew, and a nut screwed on the lead screw, the first protrusion being fixedly connected to the nut.

Preferably, the housing forms a stopper at an end of the leadscrew remote from the first moving unit, for positioning the first moving unit.

Preferably, the housing forms a block at the other end of the leadscrew adjacent the first moving unit, the leadscrew being rotatably inserted in the block.

Preferably, the first protrusion is located between the stopper and the block.

Preferably, the housing forms a flange, the flange and the second protrusion sliding into internal and external sides of the aperture and the slot, respectively, wherein when the flange slides to the bottleneck, the bottleneck expands to unlock the second protrusion from second snap.

According to a second aspect, the present invention provides an actuator of a medical device, comprising: a housing; a driving unit; a needle unit being movable relative to the housing under the driving of the driving unit, the needle unit comprising a first carriage and a needle fixed on the first carriage; a needle tube unit being movable relative to the housing under the driving of the driving unit, the needle tube unit comprising a second carriage and a needle tube fixed on the second carriage, the needle being inserted in the needle tube; a spring, two ends of the spring abutting the housing and first carriage, respectively; and a lock comprising a snap formed on one of the first and second carriages, and a protrusion formed on the other one of the first and second carriages, the protrusion being detachably engagable with the snap, wherein when the lock is locked, the protrusion engages the snap, and the first and second carriages are connected together and spaced from each other a predetermined distance; and when the lock is unlocked, the protrusion disengages from the snap, and the first and second carriages are capable of sliding relative to each other.

Preferably, another lock is formed between the driving unit and first carriage, wherein when the another lock is locked, the first carriage is connected to the driving unit and capable of being moved by the driving unit; and when the another lock is unlocked, the spring moves the first carriage relative to the housing.

Compared with the prior art, the actuator of the present invention, uses a single spring with a preloaded force to drive both the first moving unit and second moving unit, is simple in construction and convenient to use.

BRIEF DESCRIPTION OF THE DRAWINGS

A preferred embodiment of the invention will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

DETAILED DESCRIPTION OF THE PREFERRED EMBODIMENTS

Figure 7:
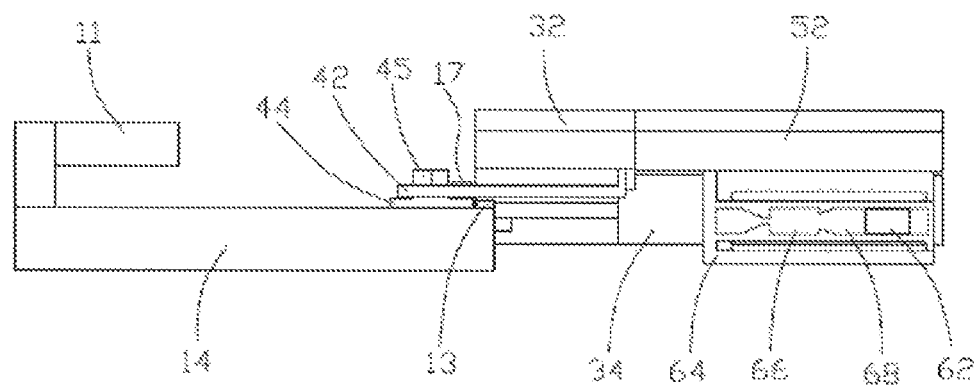
FIG. 7 shows the first lock of the actuator locked again to withdrawal the needle.
Figure 8:
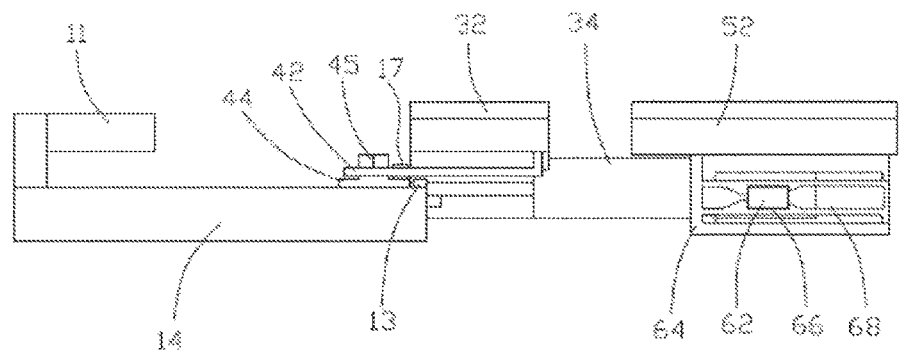
FIG. 8 shows the first lock and second lock of the actuator locked again to withdrawal the needle tube.
Figure 9:
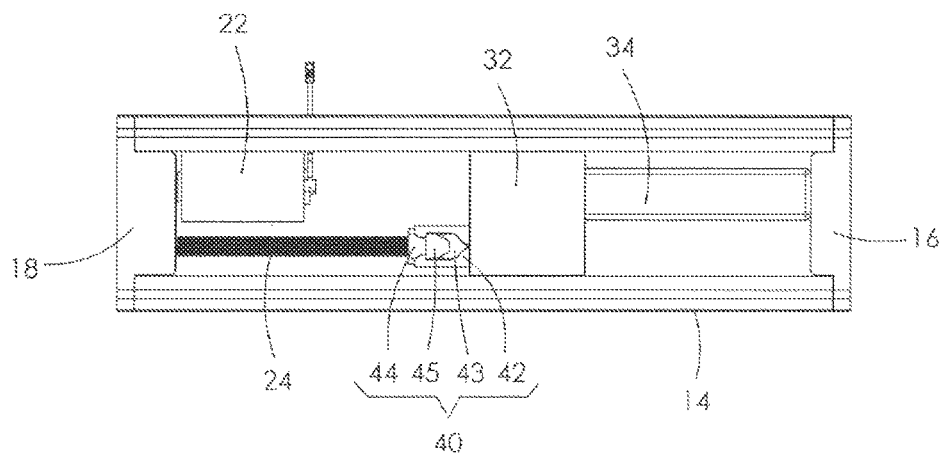
FIG. 9 shows an actuator according to an alternative embodiment of the present invention, with a cover removed.

An actuator of a medical device according to an embodiment of the present invention is shown in FIGS. 1 through 8. The actuator includes a housing 10. A driving unit 20, a first moving unit 30, a first lock 40, a second moving unit 50, a second lock 60, and a spring 70 are received in the housing 10. The spring may be in any form of elastic or resiliently deformable member which can provide a restoring force when deformed. The medical device can be liver biopsy device, surgical fastener applying apparatus, surgical removal apparatus, and etc. When the present actuator is used for a surgical fastener applying apparatus or surgical removal apparatus, the second moving unit 50 and second lock 60 can be omitted, as shown in FIG. 9.

For simplifying description of the present invention, the actuator will be described below as used in a biopsy device, as an example. As applied to liver biopsy device, the first moving unit 30 is a needle unit, the second moving unit 50 is a needle tube unit, the first lock 40 is a lock for the needle unit, and the second lock 60 is a lock for the needle tube unit. The needle and needle tube are only schematically illustrated in FIG. 4, in which a needle 31 is attached to the first carriage 32 of the needle unit 30 by a needle holder 33 and a needle tube 51 is attached to the second carriage 52 of the needle tube unit 50 by a needle tube holder 53, such that the needle and needle tube are coaxial and arranged such that the needle can pass into the needle tube, in a manner generally known. While not specifically illustrated, a needle and a needle tube may be attached to the needle unit and needle tube unit respectively in a permanent manner, for use as a disposable unit. Alternatively, to allow reuse of the actuator, the needle and needle tube may be releasably attached to the actuator.

The housing 10 includes an elongated shell 12, a frame 14 fixed in the shell 12, and front and rear covers 16, 18 connected at opposite ends of the shell 12, respectively. The shell 12 may be an aluminum extrusion. The frame 14 is similar to the shell 12 in profile, but has a length less than that of the shell 12. The frame 14 is arranged close to the rear cover 18. A mounting plate 15 extends from an end of the frame 14 which faces the rear cover 18, for mounting the driving unit 20. A stopper 11 extends from the mounting plate 15 towards an interior of the frame 14, for positioning of the needle unit 30. A block 13 and pin 17 are formed at the other end of the frame 14 which faces the front cover 16. The block 13 is aligned with the stopper 11, for positioning the first lock 40. The pin 17 is offset from the block 13, for connecting with an end of the spring 70. Preferably, the spring 70 is a coil spring.

The driving unit 20 includes a motor 22, a leadscrew 24, a gear box 26 interconnecting the motor 22 and leadscrew 24, and a nut 28 screwed on the leadscrew 24. The motor 22 and leadscrew 24 are mounted in the frame 14. The gear box 26 is arranged between the mounting plate 15 of the frame 14 and rear cover 18, and includes several gears meshed with each other. An output shaft of the motor 22 extends through the mounting plate 15 to engage an input gear of the gear box 26. One end of the leadscrew 24 extends through the mounting plate 15 to fixedly connect with an output gear of the gear box 26, and the other end of the leadscrew 24 is rotatably inserted in the block 13. The nut 28 is screwed on the leadscrew 24 and at an inner side of the block 13, thereby the block 13 not only supports rotation of the leadscrew 24, but also prevents disengagement of the nut 28 from the leadscrew 24. When the motor 22 rotates, the leadscrew 24 rotates, which makes the nut 28 move axially along the leadscrew 24.

Figure 1:
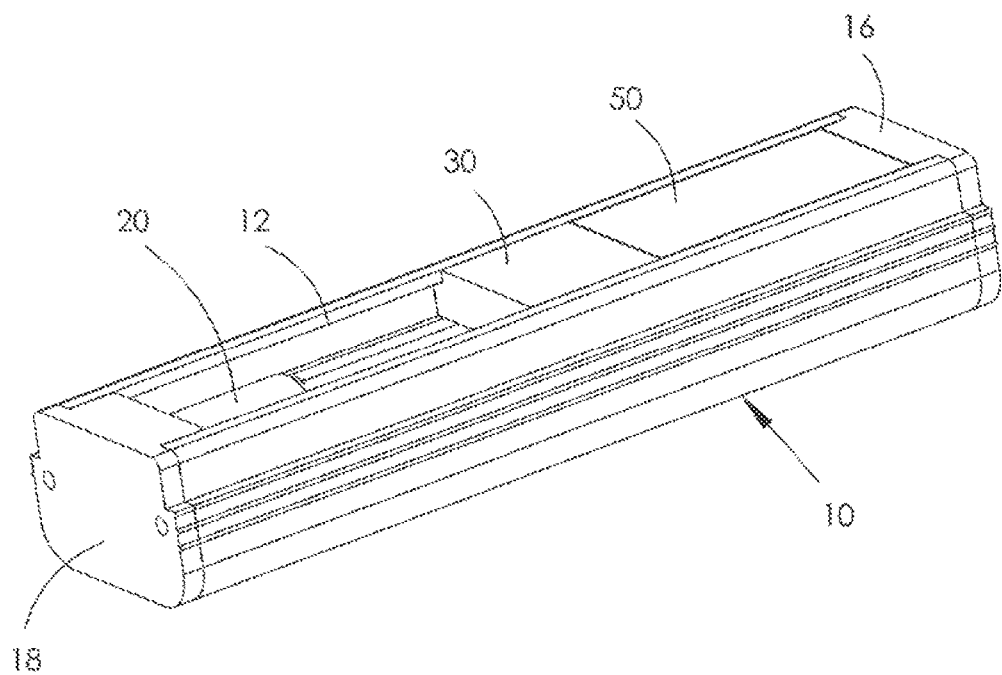
FIG. 1 is a schematic view of an actuator of a medical device according to an embodiment of the present invention.
Figure 2:
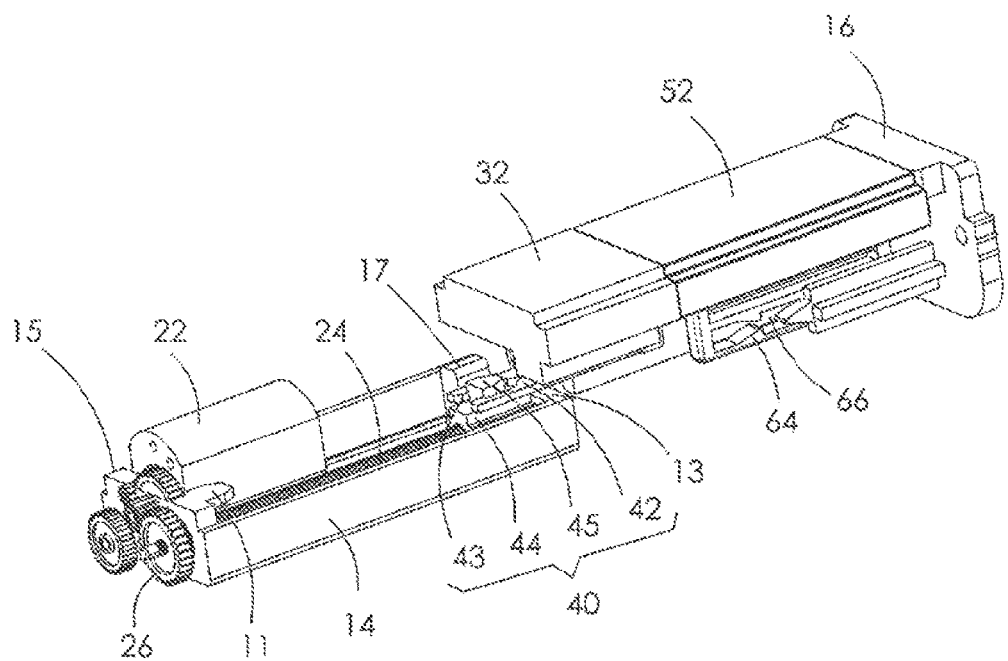
FIG. 2 shows the actuator of FIG. 1 with a housing shell and rear cover removed.
Figure 3:
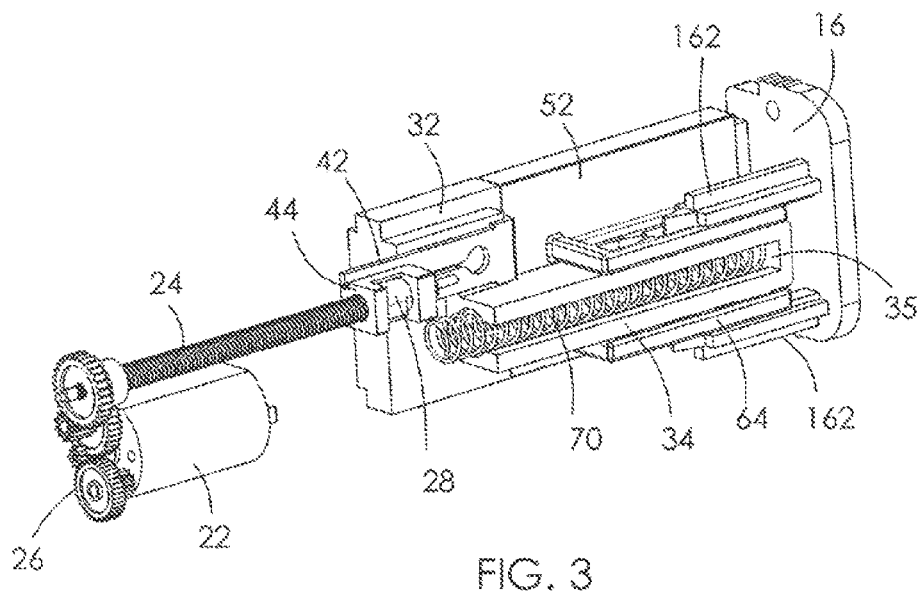
FIG. 3 is another view of FIG. 2, from a different aspect.
Figure 3A:
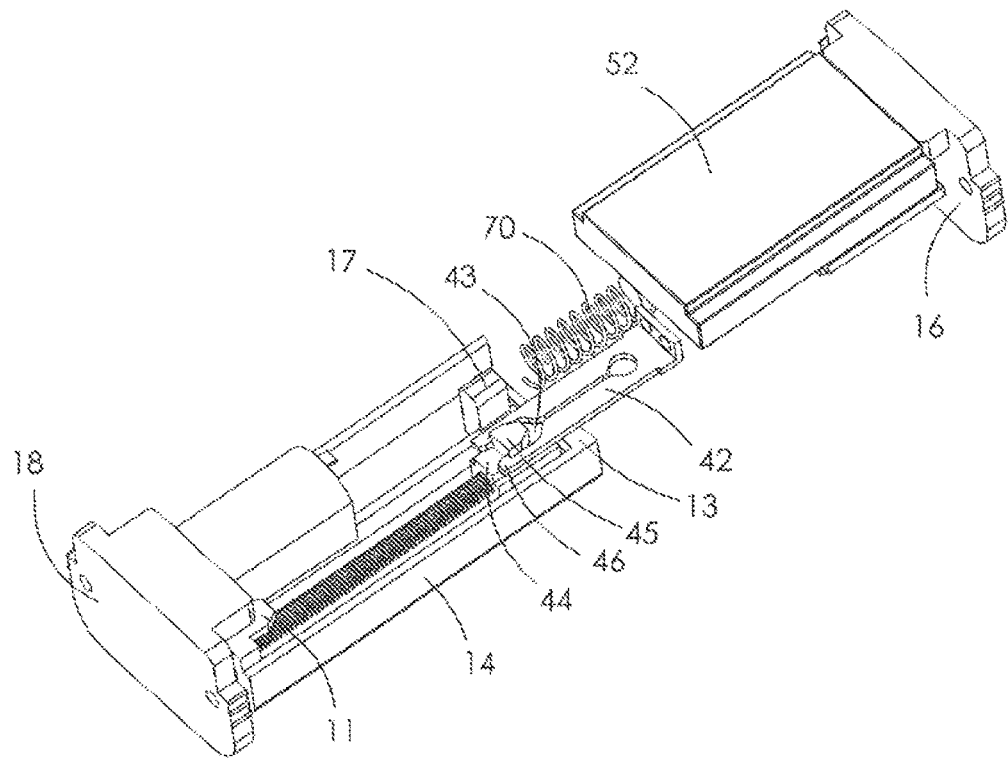
FIG. 3A is another view of FIG. 2, in which a first carriage of the actuator is omitted to show a spring inside the first carriage.
Figure 4:
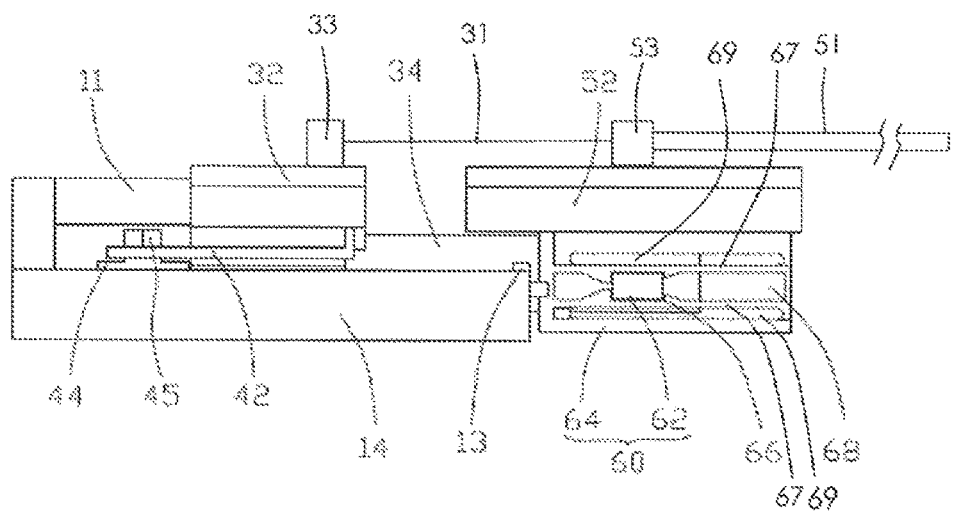
FIG. 4 shows the actuator in a home position, a first lock and a second lock thereof both being locked.
Figure 4A:
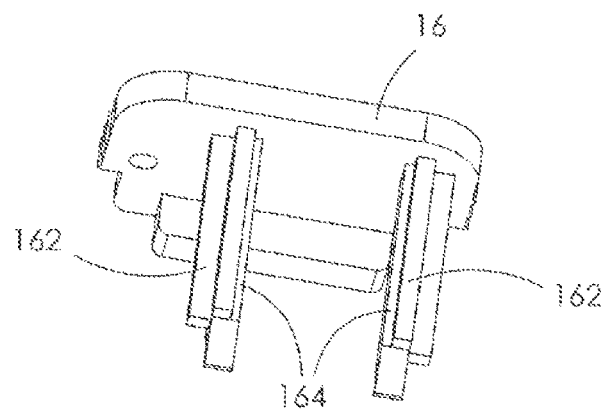
FIG. 4A illustrates a front cover of the actuator of FIG. 1.

The needle unit 30 is detachably connected to the nut 28 of the driving unit 20 through the first lock 40. The needle unit 30 includes a movable first carriage 32 and a needle 31 fixed to the first carriage 32 via a needle holder 33 (FIG. 4). A guiding rail 34 extends axially from the first carriage 32 towards the front cover 16, for connecting with the needle tube unit 50. The guiding rail 34 defines a groove 35 therein, which extends axially through an end of the first carriage 32 facing the pin 17. The spring 70 is received in the groove 35. A length of the spring 70 in natural state is not less than that of the groove 35. One end of the spring 70 abuts a closed end of the groove 35 in the guiding rail, and the other end of the spring 70 extends beyond the groove 35 to connect with or abut the pin 17, as shown in FIG. 3A, where the first carriage 32 has been omitted to show the spring 70 clearly. When the needle unit 30 moves forwards and backwards under the driving of the leadscrew 24, the spring 70 deforms by compressing or extending, as the pin 17 slides into or out of the groove 35.

The first lock 40 includes a first snap 42 fixed on the first carriage 32, and a locking member 44 mounted around the nut 28. In this embodiment, the locking member 44 is fixedly connected to the nut 28 by bolts, and moves along with the nut 28. In other embodiments, the locking member 44 can be formed with internal threads matching with the leadscrew 24, thereby integrating the nut with the locking member. Thus, the leadscrew 24 drives the locking member 44 directly, and the separate nut 28 can be omitted. A first protrusion 45 extends outwards from the locking member 44, and a hole 43 is defined in the first snap 42 corresponding to the first protrusion 45. The hole 43 extends through an end of the first snap 42 facing the first protrusion 45, thereby slitting the first snap 42 into two branches. Each of the branches forms a barb 46 at a distal end thereof. The two branches generate resilient deformation under the action of an external force, allowing the first protrusion 45 to enter or escape from the hole 43.

In this embodiment, the first snap 42 is resilient, and is separately formed and then fixedly connected to the first carriage 32 by screws. Alternatively, the first snap 42 can extend integrally from the first carriage 32. In addition, the first lock 40 is locked through engagement of the first protrusion 45 of the locking member 44 with the hole 43 of the first snap 42. It can be understood that the hole 43 can be formed in the locking member 44, while the first snap 42 forms corresponding first protrusion 45 engaging into the hole 43 of the locking member 44. Alternatively, engagement of the locking member 44 and first snap 42 can be a detachable protrusion and clasp.

Figure 4B:
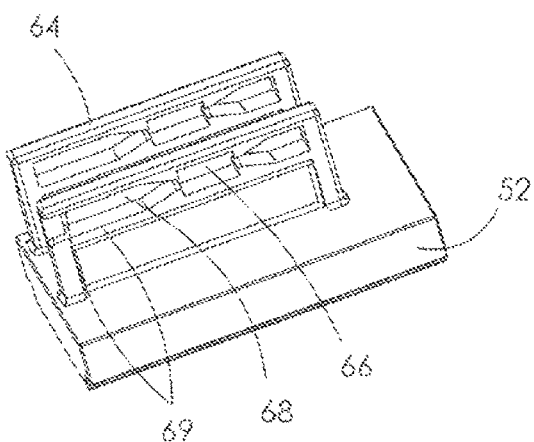
FIG. 4B illustrates a second carriage of the actuator of FIG. 1.
Figure 4C:
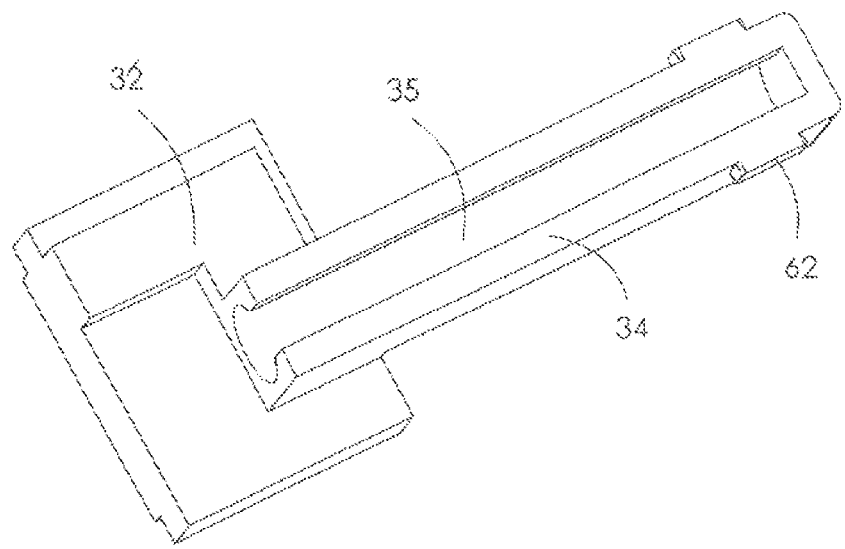
FIG. 4C illustrates the first carriage of the actuator of FIG. 1.

Referring to FIGS. 4, 4A, 4B and 4C, the needle tube unit 50 is connected to the needle unit 30 through the second lock 60. The needle tube unit 50 includes a movable second carriage 52 and a needle tube 51 fixed on the second carriage 52 via a needle tube holder 53 (FIG. 4). The needle is inserted in the needle tube. In this embodiment, the second carriage 52 is arranged on the guiding rail 34, and located between the front cover 16 and first carriage 32 of the needle unit 30. The second lock 60 includes a second protrusion 62 extending outwardly from the guiding rail 34 of the first carriage 32 (FIG. 4C) and a second snap 64 extending outwards from the second carriage 52, as shown in FIGS. 4 and 4B. The second snap 64 defines an aperture 66 and a slot 68 communicating with the aperture 66. A bottleneck is formed at the junction of the slot 68 and aperture 66 by two opposing barbs.

In detail, the slot 68 and aperture 66 are defined between two ribs 67 of the second snap 64. A narrow channel 69 is defined in the second snap 64 at an outer side of each rib 67. The channels 69 extend through the second snap 64 in a direction of thickness, which allows the ribs 67 to be resiliently deformed. The second protrusion 62 extending from the guiding rail 34 of the first carriage 32 is substantially the same size and shape as the aperture 66 of the second carriage 52. The second protrusion 62 enters into the aperture 66 to connect the first carriage 32 and second carriage 52, thereby the first and second carriages 32, 52 move together. When the second protrusion 62 disengages from the aperture 66 and enters the slot 68 under an acting force, sliding connection is formed between the first and second carriages 32, 52, i.e., the first carriage 32 is capable of sliding relative to the second carriage 52 along the guiding rail.

As shown in FIG. 4, when the present actuator is in the home position, the first lock 40 and second lock 60 both are locked and the carriages are spaced from each other. That is, the first protrusion 45 of the locking member 44 is engaged with the hole 43 of the first snap 42 of the first carriage 32, and the second protrusion 62 of the first carriage 32 is engaged with the aperture 66 of the second snap 64 of the second carriage 52. In such a position, the first carriage 32, second carriage 52, and locking member 44 are connected together. The first carriage 32 is inside the frame 14 and abuts the stopper 11. The spring 70 is preloaded, i.e., compressed. A first distance is formed between the first and second carriages 32, 52. The second carriage 52 is out of the frame 14, and spaced from the front cover 16 a second distance. The first and second distances can be designed according to need. Generally, the first distance is the depth of movement of the needle within the needle tube required to cut the lesion tissue, such as 12.1 mm, and the second distance is the depth that the needle and needle tube will be inserted into the lesion tissue of the patient body to obtain the biopsy sample, such as 26 mm.

Figure 5:
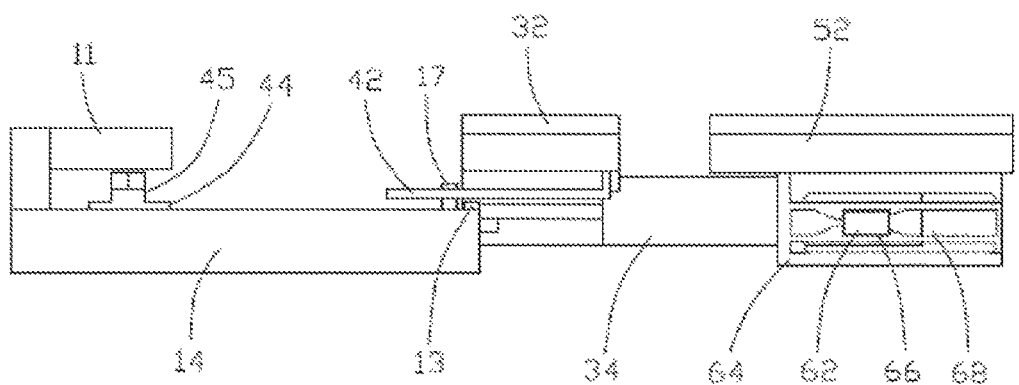
FIG. 5 shows the actuator in a ready to cut position, the first lock being unlocked.
Figure 6:
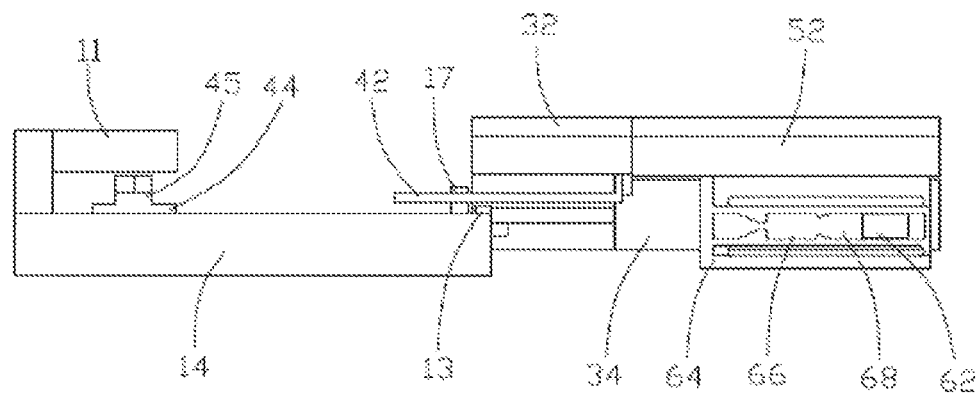
FIG. 6 shows the actuator in a tissue cut position, the second lock being unlocked.

As shown in FIG. 5, when the present driving unit 20 is in use, firstly, the needle tube and needle in the needle tube both are inserted into the patient body with a needle tip of the needle tube close to the border of the lesion tissue. Then, the motor 22 is operated to move the locking member 44 backwards to the rear cover 18 a predetermined distance. The first carriage 32, now abuts the stopper 11, which spreads the branches of the first snap 42 releasing the first protrusion from the hole 43, thereby detaching the locking member 44 from the first snap 42 of the first carriage 32. That is, the first lock 40 is unlocked. In such a state, the motor 22 is switched off. The unlocked first lock 40 allows the first carriage 32 to be moved relative to the frame 14, by the preloaded spring 70 which can now extend, pushing the first and second carriages 32, 52 towards the front cover 16.

During moving of the first and second carriages 32, 52 towards the front cover 16, the second lock 60 is kept locked, i.e., the second protrusion 62 keeps engaging with the aperture 66 of the second snap 64 until the second carriage 52 hits the front cover 16. The needle unit 30 and needle tube unit 50 move together with a length of the second distance, and correspondingly the needle and needle tube are synchronously inserted into the lesion tissue with a depth of the second distance. The needle tube covers part of the lesion tissue, and the driving unit 20 is ready to cut tissue.

When the second carriage 52 contacts the front cover 16, the needle tube unit 50 stops. The front cover 16 has a side plate 162 extending perpendicularly from an inner side thereof towards the rear cover 18. A flange 164 extends outwards from the side plate 162 corresponding to the slot 68 of the second snap 64. In this embodiment, the guiding rail 34 of the first carriage 32 has the second protrusion 62 formed at each lateral side thereof, and correspondingly the second carriage 52 forms two second snaps 64. The two second snaps 64 sandwiches the guiding rail 34 there between. Each second snap 64 matches with one corresponding second protrusion 62. The front cover 16 has two parallel side plates 162, and two flanges 164 are respectively formed on opposite sides of the side plates 162. Each flange 164 acts with one corresponding snap 64.

When the second carriage 52 hits the front cover 16, the flange 164 of the front cover 16 slides into the slot 68 and expands the bottleneck of the slot 68, which allows the second protrusion 62 to slide out of the aperture 66 to the slot 68, i.e., the second lock 60 is unlocked. Thus, under the force of the spring 70, the first carriage 32 continues to move towards the second carriage 52, and correspondingly the second protrusion 62 slides out of the aperture 66 and into the expanded slot 68. As the first carriage 32 moves towards the second carriage 52, the needle unit 30 moves relative to the needle tube unit 50 with a length of the first distance.

That is, the needle is further inserted into the lesion tissue with a depth of the first distance to cut the tissue, that is to take the biopsy sample.

After cutting the tissue, referring to FIG. 7, the motor 22 is started again to move the locking member 44 forwards to the front cover 16 until the first protrusion 45 of the locking member 44 engages the hole 43 of the first snap 42 once again. Thus, the first lock 40 is locked once again. The needle unit 30 and locking member 44 are connected. They are then moved together under the driving of the motor 22. In detail, the motor 22 is reversed to rotate the leadscrew 24 in the opposite direction to move the nut 28 towards the rear cover 18. Accordingly, the locking member 44 fixed on the nut 28 and the needle unit 30 locked with the locking member 44 move along with the nut 28 towards the rear cover 18 with a length of the first distance, while the needle tube unit 50 remains stationary. That is, the needle unit 30 moves relative to the needle tube unit 50 with a length of the first distance, which makes the second protrusion 62 enter the aperture 66 of the second snap 64. Accordingly, the second lock 60 is locked once again to connect the needle unit 30 and needle tube unit 50 together, as shown in FIG. 8. In such a state, the needle moves out from the lesion tissue with a depth of the first distance. The spring 70 is compressed again by the movement of the needle unit 30.

Then, under the driving of the motor 22, the connected needle unit 30 and needle tube unit 50 move together towards the rear cover 18 with a length of the second distance. Accordingly, the needle and needle tube move out together from the lesion tissue with a depth of the second distance to the border of the lesion tissue. Then, the doctor can move out the needle and needle tube from the patient's body. In such a state, the needle unit 30, needle tube unit 50, first lock 40, second lock 60, and the spring 70 return to home position shown in FIG. 4, facilitating the taking of another biopsy sample.

For the embodiment of the present invention described above, a single driving unit 20 and a single preloaded spring 70 can drive both the first moving unit 30 and second moving unit 50, which can be used repeatedly, is safe and reliable, and is simple in operation.

In the description and claims of the present application, each of the verbs "comprise", "include", "contain" and "have", and variations thereof, are used in an inclusive sense, to specify the presence of the stated item or feature but do not preclude the presence of additional items or features.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of example only, and various other modifications will be apparent to persons skilled in the field without departing from the scope of the invention as defined by the appended claims.

For example, the driving unit 20 may drive the leadscrew 24 to rotate reversely by other ways, such as changing the gearbox, etc. In addition, the spring 70 can be any deformable element, not limited to a coil spring. Further, the flanges 164 of the side plates 162 of the front cover 16 can be omitted, and thus the first and second moving units 30, 50 move together.

The invention claimed is:

1. An actuator of a medical device, comprising:
 a housing;
 a driving unit mounted in the housing;
 a first moving unit mounted in the housing and being capable of sliding relative to the housing under the driving of the driving unit, the first moving unit comprising a movable first carriage;
 a spring with two ends thereof lies against the housing and first carriage, respectively; and
 a first lock formed between the driving unit and first carriage, the first lock comprising a first snap and a first protrusion being horizontally detachably engagable in the first snap, one of the first snap and first protrusion being formed on the first carriage, and the other one of the first snap and first protrusion being formed on the driving unit;
 wherein when the first protrusion disengages from the first snap, the spring moves the first carriage relative to the housing;
 a second moving unit being capable of sliding relative to housing, the second moving unit comprising a movable second carriage, a second lock formed between the first and second carriages, the second lock comprising a second protrusion formed on one of the first and second carriages, and a second snap formed on the other one of the first and second carriages, the second protrusion being detachably engagable in the second snap,
 wherein when the second protrusion is engaged with the second snap, the first and second carriages are connected together and spaced from each other a predetermined distance; and when the second protrusion is disengaged from the second snap, the first and second carriages can slide relative to each other.

2. The actuator of claim 1, wherein the second snap defines an aperture and a slot communicating with the aperture, the slot extending along a deformation direction of the spring, a bottleneck being formed at a junction of the aperture and slot, wherein when the second protrusion is engaged with the second snap, the second protrusion is captured within the aperture; and when the second protrusion is disengaged from the second snap, the second protrusion is disposed in the slot.

3. The actuator of claim 1, wherein the housing forms a pin, a guiding rail extends from the first carriage, the guiding rail defines a groove which extends in the deformation direction of the spring and through one end of the guiding rail facing the pin, the spring is received in the groove, a length of the spring is not less than that of the groove, one end of the spring abuts the pin, and the other end of the spring abuts a closed end of the groove in the guiding rail.

4. The actuator of claim 3, wherein the driving unit comprises a motor, a leadscrew, and a gear box connected between the motor and the leadscrew, the other one of the first snap and first protrusion being screwed on the leadscrew.

5. The actuator of claim 3, wherein the driving unit comprises a motor, a leadscrew, a gear box connected between the motor and leadscrew, and a nut screwed on the lead screw, the first protrusion being fixedly connected to the nut.

6. The actuator of claim 5, wherein the housing forms a stopper at an end of the leadscrew remote from the first moving unit, for positioning the first moving unit.

7. The actuator of claim 6, wherein the housing forms a block at the other end of the leadscrew adjacent the first moving unit, the leadscrew being rotatably inserted in the block.

8. The actuator of claim 7, wherein the first protrusion is located between the stopper and the block.

9. The actuator of claim 2, wherein the housing forms a flange, the flange and the second protrusion sliding into internal and external sides of the aperture and the slot, respectively, wherein when the flange slides to the bottleneck, the bottleneck expands to unlock the second protrusion from second snap.

10. An actuator of a medical device, comprising:
a housing;
a driving unit;
a needle unit being movable relative to the housing under the driving of the driving unit, the needle unit comprising a first carriage and a needle fixed on the first carriage;
a needle tube unit being movable relative to the housing under the driving of the driving unit, the needle tube unit comprising a second carriage and a needle tube fixed on the second carriage, the needle being inserted in the needle tube;
a spring, two ends of the spring lies against the housing and first carriage, respectively; and
a lock comprising a snap formed on one of the first and second carriages, and a protrusion formed on the other one of the first and second carriages, the protrusion being horizontally detachably engagable with the snap, wherein when the lock is locked, the protrusion engages the snap, and the first and second carriages are connected together and spaced from each other a predetermined distance; and when the lock is unlocked, the protrusion disengages from the snap, and the first and second carriages are capable of sliding relative to each other.

11. The actuator of claim 10, further comprising another lock formed between the driving unit and first carriage, wherein when the another lock is locked, the first carriage is connected to the driving unit and capable of being moved by the driving unit; and when the another lock is unlocked, the spring moves the first carriage relative to the housing.

* * * * *